United States Patent [19]

Eickel

[11] 4,147,936
[45] Apr. 3, 1979

[54] METHOD OF MAKING TOMOGRAPHIC IMAGES OF X-RAYED OBJECTS

[75] Inventor: Rolf Eickel, München, Fed. Rep. of Germany

[73] Assignee: AGFA-Gevaert AG, Leverkusen, Fed. Rep. of Germany

[21] Appl. No.: 866,035

[22] Filed: Dec. 30, 1977

[30] Foreign Application Priority Data

Jan. 7, 1977 [DE] Fed. Rep. of Germany ....... 2700364

[51] Int. Cl.$^2$ ...................... G01N 21/34; G01N 23/04
[52] U.S. Cl. ................................. 250/445 T; 250/491
[58] Field of Search ............... 250/445 T, 315, 315 A, 250/358 R, 358 T, 490, 491

[56] References Cited

U.S. PATENT DOCUMENTS 4,055,767 10/1977 Allemand .............................. 250/385
4,087,694 5/1978 Hellstrom ............................. 250/491

*Primary Examiner*—Craig E. Church
*Assistant Examiner*—Thomas P. O'Hare
*Attorney, Agent, or Firm*—Peter K. Kontler

[57] ABSTRACT

A tomographic image of a selected layer of a stationary object is made by moving the source of X-rays along a first path at one side of the selected layer and by moving an ionography imaging chamber which contains a dielectric receptor sheet along a second path at the other side of the selected layer. The movement of the sheet is synchronized with movement of the source of X-rays and includes a translatory movement in a direction counter to the direction of movement of the source, a pivotal movement to maintain the sheet in a plane which is normal to the central beam of the bundle of X-rays, and a sidewise movement to vary the distance between the selected layer and the sheet so that the length of the projection of selected layer upon the sheet remains unchanged. If the sheet is rectangular, the pivotal movement is performed about an axis which is located in the plane of the selected layer and is parallel to the shorter sides of the sheet.

10 Claims, 4 Drawing Figures

METHOD OF MAKING TOMOGRAPHIC IMAGES OF X-RAYED OBJECTS

BACKGROUND OF THE INVENTION

The present invention relates to roentgenography in general, and more particularly to tomography, i.e., to a procedure of making a detailed X-ray image of details in a selected plane of an object located between the source of X-rays and the charge-receiving material which is to be exposed to object-modulated X-rays. Still more particularly, the invention relates to the making of tomographic images of X-rayed objects by resorting to sheet-like receptors which are confined in the gas-filled interelectrode gap of an ionography imaging chamber during exposure to a pattern of X-rays.

A normal (i.e., conventional) X-ray image furnishes the sum of absorption differences of all layers or strata of an object which is located between the source of X-rays and the charge-receiving sheet. On the other hand, a tomographic image furnishes sharp details of a single stratum of the X-rayed object. The thickness of the selected stratum can be varied within a reasonably wide range. The details in the other stratum or strata of the object are blurred.

In making a conventional tomographic image, the object is stationary while the source of X-rays and the X-ray film are moved relative to the object and relative to each other (in opposite directions) in such a way that portions of a selected layer of the object are imaged on the same portion of the film. The images of portions of other layers of the object constantly change their positions relative to the film so that the outlines of images of such portions are unsharp. Presently known tomographic apparatus are operated to continuously change the angle between the central beam of the bundle of X-rays and the film plane. This does not appreciably affect the quality of images which are exposed onto a silver-containing photosensitive layer. However, if the film is replaced with a sheet-like receptor of object-modulated X-rays which is confined in the interelectrode gap of an ionography imaging chamber, the sharpness of the tomographic image is highly unsatisfactory. This is due to the fact that the width of the interelectrode gap is normally in the range of one centimeter. Thus, when the inclination of the gap with respect to the selected layer of the object changes (simultaneously with changes in the direction of penetration of X-rays), the X-rays generate ion trails which are not parallel to the electric field that develops between the electrodes of the ionography imaging chamber. Consequently, each spot or unit area of the selected layer of the object is imaged in the form of a line.

OBJECTS AND SUMMARY OF THE INVENTION

An object of the invention is to provide a novel and improved tomographic method which renders it possible to obtain sharp images of selected layers or strata of objects which are imaged onto receptors in the interelectrode gap of an ionography imaging chamber.

Another object of the invention is to provide a tomographic method which can be practiced by resorting to presently known ionography imaging chambers.

A further object of the invention is to provide a relatively simple tomographic method which, even though utilizing ionography imaging chambers, can produce images of selected strata which are just as satisfactory as tomographic images exposed on silver-containing photosensitive layers.

An additional object of the invention is to provide a tomographic method which insures the making of sharp images of selected strata of an X-rayed object irrespective of whether the source of X-rays and the receptor sheet are moved along straight or along arcuate paths.

The invention is embodied in a method of making a tomographic image of a selected layer or stratum of an object (e.g., a portion of the body of a patient) which is disposed between a suitable source of a bundle of X-rays (including a central beam) and a dielectric receptor sheet which is confined in the gas-filled interelectrode gap of an ionography imaging chamber. The object is normally stationary.

The method comprises the steps of moving the source of X-rays in a first direction along a first path at one side of the selected layer or stratum, and moving the imaging chamber (with the receptor sheet therein) in synchronism with the source of X-rays along a second path at the other side of the selected layer. The step of moving the imaging chamber includes imparting to the imaging chamber a translatory movement in a second direction counter to the first direction, pivoting the imaging chamber about an axis which is located in the plane of the selected layer to thereby maintain the dielectric sheet in a plane which is normal to the central beam of the bundle of X-rays, and varying the distance between the dielectric sheet and the selected layer so that the length of the projection of the layer into the plane of the sheet remains at least substantially unchanged.

As a rule, the sheet is substantially rectangular. If the ionography imaging chamber contains a rectangular sheet, the aforementioned axis is preferably parallel to the shorter sides of the sheet; this also contributes to sharpness of the tomographic image.

The first mentioned moving step preferably comprises maintaining the central beam of the bundle of X-rays at right angles to the aforementioned axis of pivotal movement of the sheet.

The first path may be parallel to the plane of the selected layer. This necessitates a first type of movement of the dielectric sheet for the purpose of changing the distance between the sheet and the selected layer.

If the first path is an arcuate path whose center of curvature is located on the aforementioned axis, the step of changing the distance between the dielectric sheet and the selected layer is carried out in a somewhat different way.

The novel features which are considered as characteristic of the invention are set forth in particular in the appended claims. The improved method itself, however, together with additional features and advantages thereof, will be best understood upon perusal of the following detailed description of certain specific embodiments with reference to the accompanying drawing.

DESCRIPTION OF THE PREFERRED EMBODIMENTS

Figure 1:
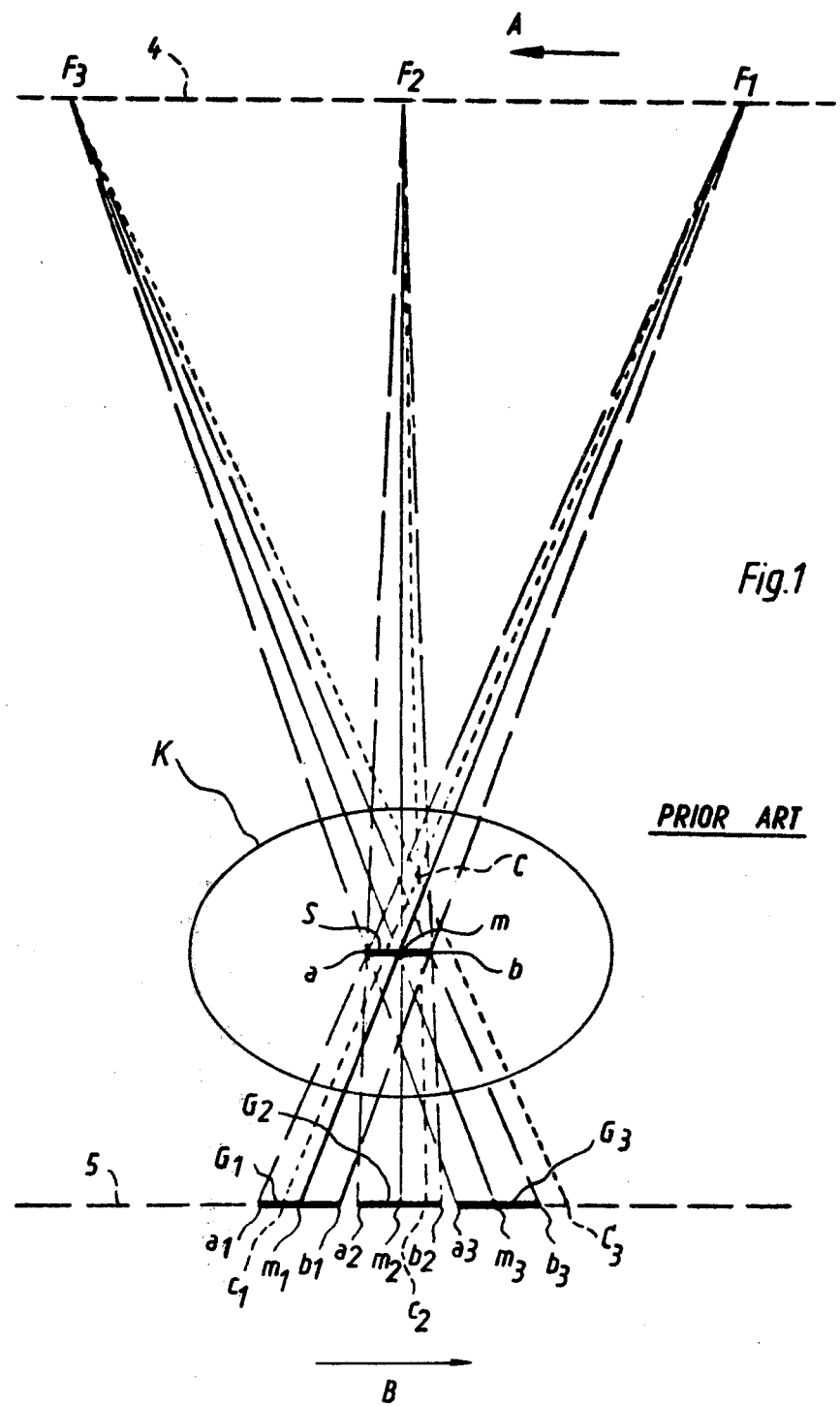
FIG. 1 is a diagrammatic view of certain parts of an apparatus which can be utilized for the practice of a conventional tomographic method.

FIG. 1 illustrates the essential constituents of an apparatus for the practice of a conventional tomographic method of the type described, for example, by Grossmann in the German publication entitled "Fortschritte auf dem Gebiete der Röntgenstrahlen" (Vol. 51, 1935, pages 61 and 191). The selected layer or stratum of the object K is shown at S, the center of a source of X-rays is shown at F, and the reference character G denotes a conventional X-ray film. Three different positions of the center F and of the film G are respectively shown at $F_1$, $F_2$, $F_3$ and $G_1$, $G_2$, $G_3$.

In order to make a tomographic image, the center F is moved continuously along a first straight path denoted by the line 4, and the film G is moved continuously along a second straight path denoted by the line 5, always in synchronism with the center F. The center F and the film G are moved in opposite directions (see the arrows A and B). It will be noted that the unit areas or points a, b and m of the selected layer S are always imaged on the same portions of the film F. The images of the unit area a in the positions $F_1$, $F_2$ and $F_3$ of the film F are respectively shown at $a_1$, $a_2$ and $a_3$. Analogously, the images of unit areas b and m (in the positions $G_1$, $G_2$ and $G_3$ of the film G) are respectively shown at $b_1$, $b_2$, $b_3$ and $m_1$, $m_2$, $m_3$. Thus, the method results in the making of a sharp image of the selected layer S. The unit area c of a layer which does not coincide with the selected layer S is imaged on different portions of the film G (see the images $c_1$ and $c_2$ in the positions $G_1$ and $G_2$, respectively). When the film moves to the position $G_3$, the image ($c_3$) of the unit area c is located outside of the confines of the photosensitive layer. At any rate, the image of the unit area c is blurred.

Figure 2:
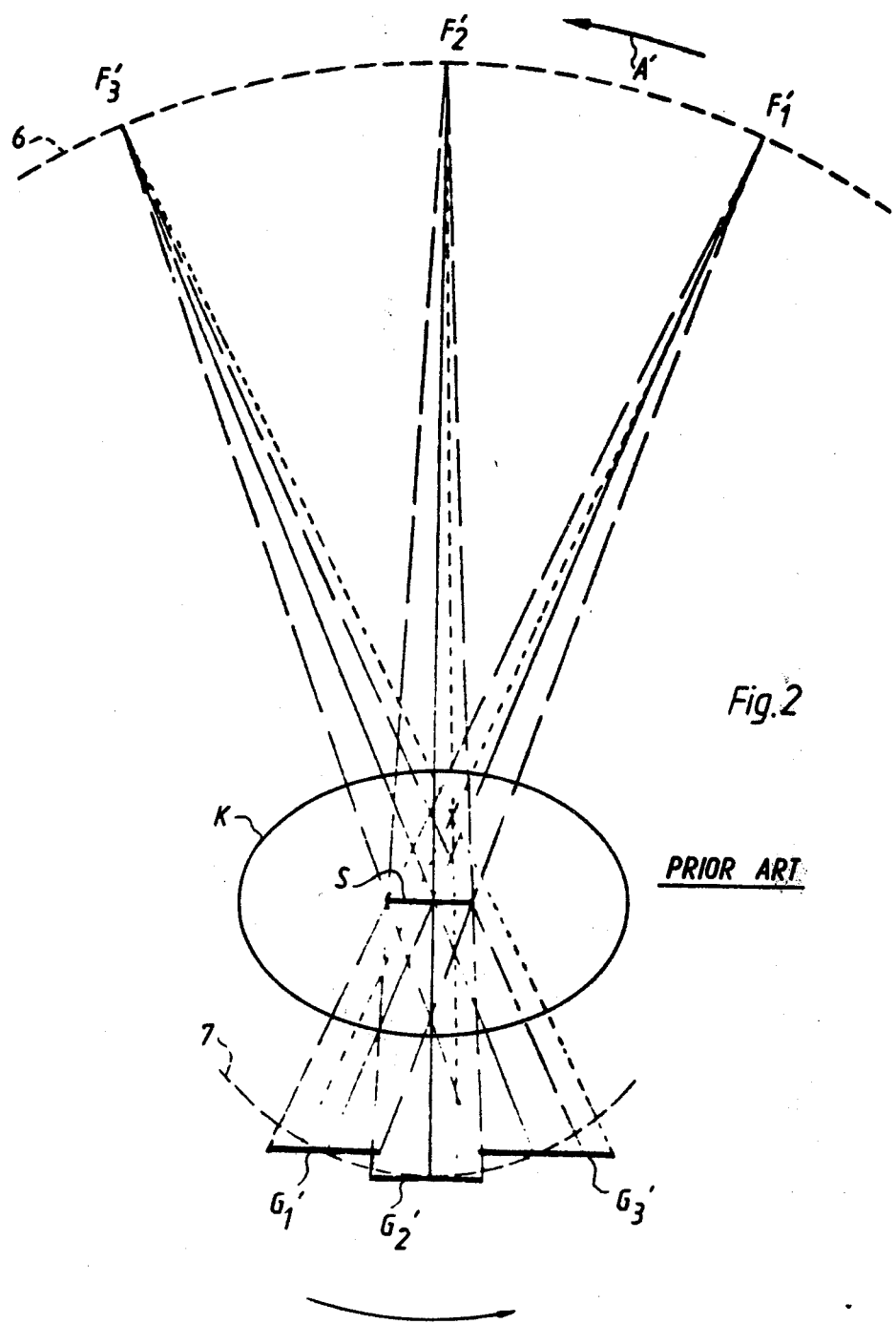
FIG. 2 is a similar diagrammatic view of an apparatus for the practice of a second conventional method.

FIG. 2 shows a second conventional tomographic technique. The center F' of the source of X-rays is moved along an arcuate path (line 6) in the direction of arrow A', and the film G' is moved along an arcuate path (line 7) while remaining parallel to the selected stratum or layer S of the object K. Three different positions of the center F' and film G' are respectively shown at $F_1'$, $F_2'$, $F_3'$ and $G_1'$, $G_2'$, $G_3'$. The centers of curvature of the arcuate paths denoted by the lines 6 and 7 are located in the plane of the layer S.

Figure 3:
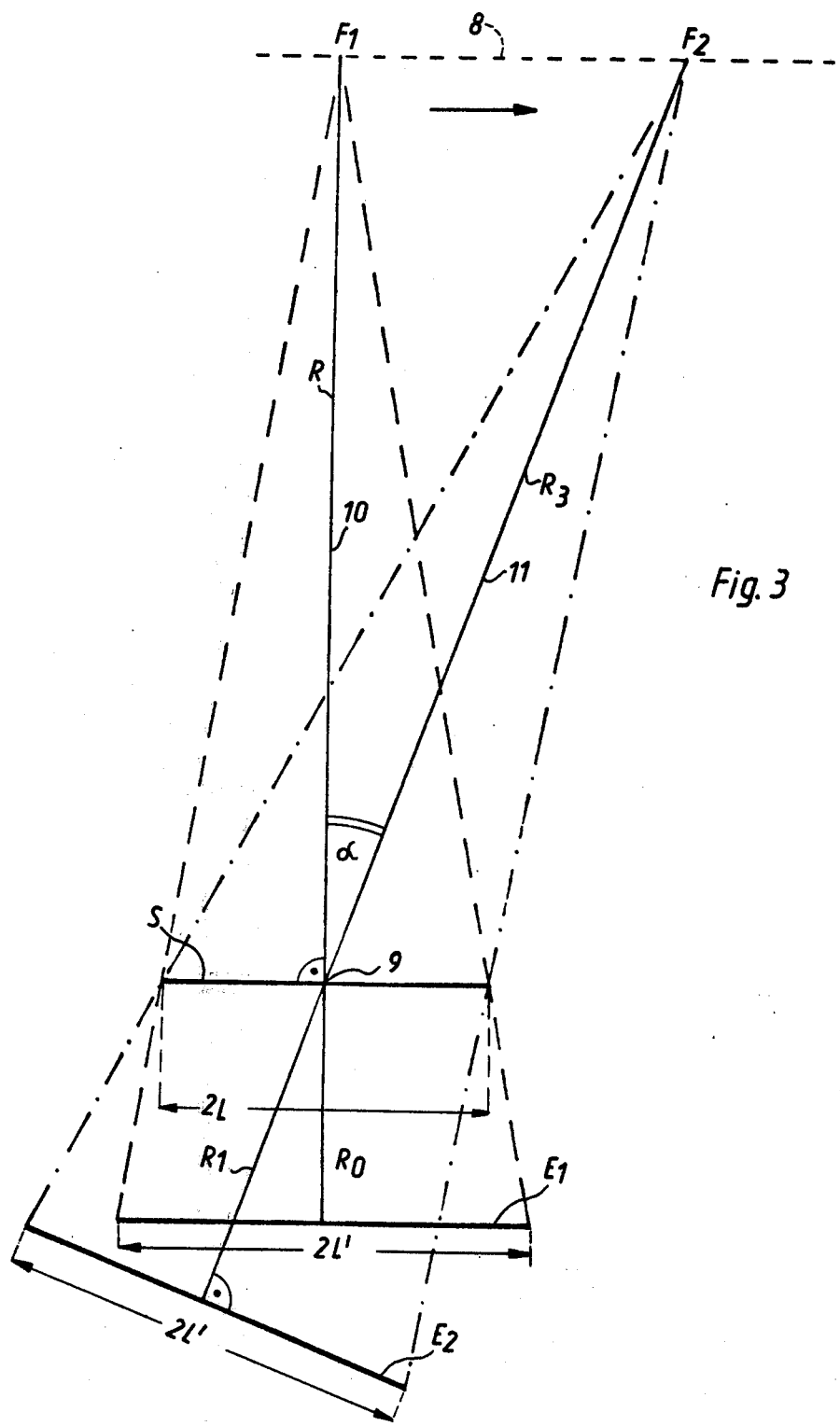
FIG. 3 is a diagram of certain parts of an apparatus which can be used to practice a method embodying one form of the present invention.

FIG. 3 represents one embodiment of the improved tomographic technique. The selected layer or stratum of an object is shown at S, the reference characters $F_1$ and $F_2$ denote two positions of the center of a source of X-rays, and the reference characters $E_1$ and $E_2$ designate two positions of the dielectric receptor sheet in the interelectrode gap of an ionography imaging chamber. The straight path of movement of the center of the source of X-rays is denoted by the broken line 8 which is parallel to the layer S. The length of the layer S (as measured in the direction of movement of the center) equals 2L. The central beams 10, 11 of the bundle of X-rays in the positions $F_1$ and $F_2$ of the center make an acute angle alpha. The central beams 10 and 11 intersect each other in the centrum of the layer S; the axis 9 where the beams 10, 11 intersect in the plane of the layer S is normal to the plane of FIG. 3.

When the center of the source of X-rays assumes the position $F_1$, the beam 10 is normal to the plane of the layer S and the dielectric receptor sheet (in the position $E_1$) is parallel to the layer S. The distance between the planes of the layer S and sheet E (in the position $E_1$) equals $R_0$, and the distance between the axis 9 and center F (in the position $F_1$) equals R. The length of the image of the layer S on the receptor sheet (in the position $E_1$) equals 2L'.

When the center of the source of X-rays is moved to the position $F_2$, the dielectric sheet is moved to the position $E_2$ in which the length of the image of the layer S on the dielectric sheet again equals 2L'. The distance between the centrum of the layer S and the centrum of the sheet (in the position $E_2$) increases from $R_0$ to $R_1$, and the distance between the axis 9 and the center F (in the position $F_2$) increases from R to $R_3$.

The movement of the sheet from the position $E_1$ to the position $E_2$ is a composite movement which is composed of a translatory movement counter to the direction of movement of the center F from the position $F_1$ to the position $F_2$, a pivotal movement which insures that the plane of the sheet remains normal to the central beam (11 when the center F assumes the position $F_2$), and a sidewise movement in a direction away from the layer S (namely, in the direction of propagation of the central beam of the bundle of X-rays). The last-mentioned movement causes the distance between the axis 9 and the center of the sheet to increase from $R_0$ to $R_1$. Such movement is necessary in order to insure that the length (2L') of the image of the layer S on the sheet remains unchanged. In the absence of the third movement, the change of inclination of the central beam during movement of center F from the position $F_1$ to the position $F_2$ would result in a shortening of the projection of the layer S on the plane of the sheet.

The distance $R_1$ is a function of the angle alpha and can be expressed as follows:

$$R_1 = \left| \frac{(R+R_0)(L^2\sin^2\alpha - R^2/\cos^2\alpha)}{R^2} \right| - \frac{R}{\cos\alpha}.$$

This equation can be resorted to for calculation of any desired number of positions of the sheet with respect to the selected layer S in order to insure that the means which guides the ionography imaging chamber during movement of the center F along the path denoted by the line 8 enables the sheet to assume positions in each of which the length (2L') of the image of the layer S' is the same.

Figure 4:
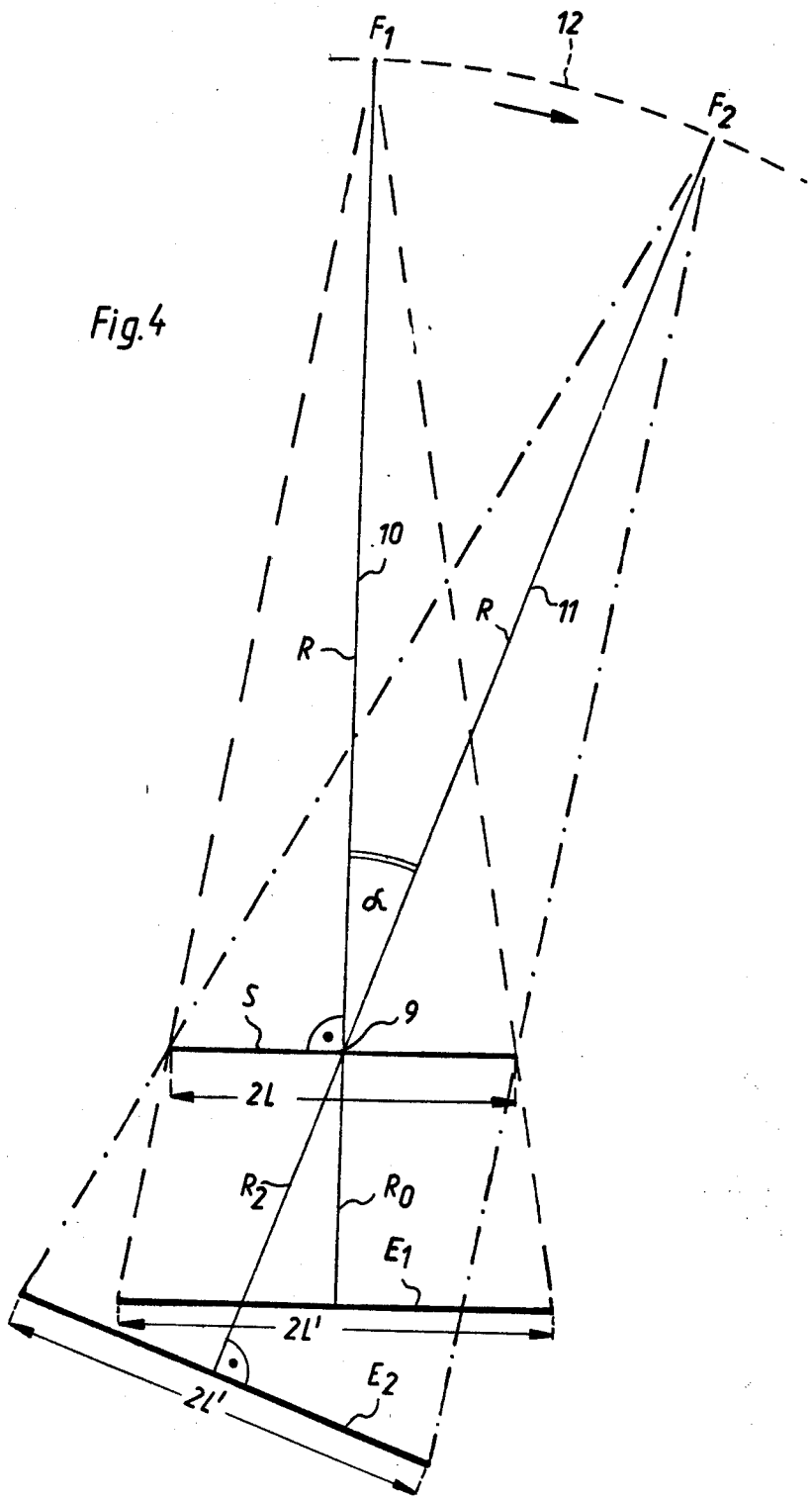
FIG. 4 is a similar diagram of certain parts of an apparatus which can be used for the practice of a modified method embodying the invention.

FIG. 4 shows a second embodiment of the improved tomographic technique. The difference between the techniques of FIGS. 3 and 4 is that the center F moves along an arcuate path designated by the line 12 so that the distance between F and 9 (in the positions $F_1$ and $F_2$ as well as any further positions of F) always equals R (R is the radius of curvature of the path 12). The distance between the axis 9 and the center of the sheet (in the position $E_2$) equals $R_2$. This distance (as well as any other distance between the axis 9 and the center of the dielectric sheet in additional positions of the sheet) can be calculated as follows:

$$R_2 = \left| \frac{(R+R_0)(L^2\sin^2\alpha - L^2)}{R^2 \cdot \cos\alpha} \right| - R.$$

It will be noted that $R_2$ is again a function of the angle alpha. The composite movement of the sheet (i.e., of the ionography imaging chamber) is again composed of a translatory movement counter to the direction of movement of the center F, a pivotal movement about the axis 9, and a sidewise movement away from the layer S (such sidewise movement must be carried out with a view to satisfy the above equation for $R_2$).

It will be noted that, in each embodiment of the improved method, the entire bundle of X-rays impinges upon the sheet substantially at right angles independently of the angle alpha. Therefore, the bundle of object-modulated X-rays is always normal or substantially normal to the electrodes which define the gas-filled gap of the ionography imaging chamber. The electrodes are parallel or nearly parallel to the plane of the sheet. All this insures that one obtains a sharp image of the selected layer S, i.e., the effect of the fact that the inclination of X-rays with respect to the layer S changes upon the quality of the image is much less pronounced than if the ionography imaging chamber were moved in the same way as the film G or G'.

It is presently preferred to employ relatively small dielectric receptor sheets. For example, if the format of the sheet is 13×18 cm, the distance R will equal 109 cm and the distance $R_0$ will equal 34 cm. Furthermore, and since the sheet is normally rectangular, the axis 9 is preferably parallel to the two shorter sides of the sheet; this further reduces the likelihood of making a blurred image of the selected layer S.

The imaging of a selected layer can be improved still further by resorting to an ionography imaging chamber which is curved in such a way (in a manner known per se) that the center of its curvature coincides with the center of the source of X-rays. This insures that each and every ray of the bundle of X-rays issuing from the source makes a right angle with the respective portion of the dielectric sheet (whose curvature then matches the curvature of electrodes in the imaging chamber). The same (or a similar) result can be achieved by resorting to a flat imaging chamber with virtual electrodes which cause the electric field lines to conform to the direction of impingement of X-rays in each position of the source. Reference may be had to U.S. Pat. No. 3,859,529 granted Jan. 7, 1975 to Proudian et al. A suitable ionography imaging chamber with a flat dielectric receptor sheet is further shown in commonly owned U.S. Pat. No. 4,021,668 granted May 3, 1977 to Pfeifer et al. The manner in which the interelectrode gap can be filled with compressed high Z gas is disclosed, for example, in commonly owned copending application Serial No. 720,577 filed Sept. 7, 1976 by Müller et al., now U.S. Pat. No. 4,074,133 granted Feb. 14, 1978.

An important advantage of the improved method is that it can be practiced by resorting to ionography imaging chambers and that resort to such chambers does not result in the making of lower-quality tomographic images. All that is necessary is to insure that the movement of imaging chamber (in synchronism with movement of the source of X-rays) satisfies the requirement that the length of the image of a selected layer of an object on the dielectric receptor sheet remains unchanged while the source and the sheet move relative to the object as well as with respect to each other. Also, the X-rays should make a right angle (or an angle approximately 90 degrees) with the plane of the dielectric sheet in each position of the imaging chamber. As mentioned above, the movement of dielectric sheet away from the selected plane (while the center F moves from the position $F_1$ in which the central beam of the bundle of X-rays is normal to the plane of the layer S) insures that the reduction of projection of the layer S' into the plane of the sheet E does not result in a reduction of the size of the image.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed is:

1. A method of making a tomographic image of a selected layer of an object which is disposed between a source of a bundle of X-rays, including a central beam, and a dielectric receptor sheet which is confined in the gas-filled interelectrode gap of an ionography imaging chamber, comprising the steps of moving the source of X-rays in a first direction along a first path at one side of said layer; and moving the imaging chamber in synchronism with the source along a second path at the other side of said layer, including imparting to the chamber a translatory movement in a second direction counter to said first direction, pivoting the chamber about an axis which is located in the plane of said layer to thereby maintain the sheet in a plane which is normal to the central beam of said bundle, and varying the distance between the sheet and said layer so that the length of the projection of said layer into the plane of the sheet remains unchanged.

2. A method as defined in claim 1, wherein the sheet is substantially rectangular and said axis is parallel to the shorter sides of the sheet.

3. A method as defined in claim 1, wherein said first mentioned moving step includes maintaining said central beam at right angles to said axis.

4. A method as defined in claim 1, wherein said first path is parallel to the plane of said layer and the angle which said central beam makes with the plane of said layer varies as a result of movement of said source along said first path.

5. A method as defined in claim 4, wherein said distance varying step includes changing the spacing between the sheet and said layer as a function of changes of the angle between said central beam in a first position in which the latter is normal to said layer and said central beam in any position other than said first position, the spacing between the sheet and said layer in each of said other positions satisfying the equation $$R_1 = \left| \frac{(R+R_0)(L^2\sin^2\alpha - R^2/\cos^2\alpha)}{R^2} \right| - \frac{R}{\cos\alpha},$$

wherein $R_1$ is the distance between the sheet and said layer in one of said other positions of said central beam, R is the distance between said first path and said layer in said first position of said central beam, $R_0$ is the distance between the sheet and said layer in said first position of said central beam, and alpha is said angle in said one other position of said central beam.

6. A method as defined in claim 5, wherein said layer is parallel to the sheet in said first position of said central beam.

7. A method as defined in claim 1, wherein said first path is an arcuate path and the center of curvature of said first path is located on said axis.

8. A method as defined in claim 7, wherein the angle which said beam makes with the plane of said layer varies as a result of movement of said source along said first path, said distance varying step including changing the spacing between the sheet and said layer as a function of changes of the angle between the central beam in a first position in which the latter is normal to the plane of said layer and said central beam in any position other than said first position, the spacing between the sheet and said layer in each of said other positions satisfying the equation $$R_2 = \left| \frac{(R+R_0)(L^2\sin^2\alpha - R^2)}{R^2\cos\alpha} \right| - R,$$

wherein $R_2$ is the distance between the sheet and said layer in one of said other positions of said central beam, R is the radius of curvature of said first path, $R_0$ is the distance between said layer and the sheet in said first position of said central beam, L is one half the length of said layer, and alpha is said angle in said one other position of said central beam.

9. A method as defined in claim 8, wherein said layer is parallel to the sheet in said first position of said central beam.

10. A method as defined in claim 1, wherein the sheet in said gap is flat.

* * * * *